United States Patent [19]
Klintz et al.

[11] Patent Number: 5,698,494
[45] Date of Patent: Dec. 16, 1997

[54] SUBSTITUTED N-PHENYLGLUTARIMIDES AND N-PHENYLGLUTARAMIDES, THEIR PREPARATION AND USE

[75] Inventors: Ralf Klintz, Dannstadt-Schauernheim; Gerhard Hamprecht, Weinheim; Elisabeth Heistracher, Ludwigshafen; Peter Schaefer, Bad Duerkheim; Uwe Kardorff, Mannheim; Karl-Otto Westphalen, Speyer; Matthias Gerber, Limburgerhof; Helmut Walter, Obrigheim, all of Germany

[73] Assignee: BASF Aktiengesellschaft, Ludwigshafen, Germany

[21] Appl. No.: 428,107

[22] PCT Filed: Oct. 19, 1993

[86] PCT No.: PCT/EP93/02879
§ 371 Date: Apr. 26, 1995
§ 102(e) Date: Apr. 26, 1995

[87] PCT Pub. No.: WO94/10147
PCT Pub. Date: May 11, 1994

[30] Foreign Application Priority Data

Oct. 31, 1992 [DE] Germany ............ 42 36 880.4

[51] Int. Cl.$^6$ ............ A01N 43/40; C07D 211/40; C07D 401/10
[52] U.S. Cl. ............ 504/167; 546/219
[58] Field of Search ............ 546/219; 504/167

[56] References Cited

U.S. PATENT DOCUMENTS

| | | | |
|---|---|---|---|
| 3,655,669 | 4/1972 | Ackerman | 546/220 |
| 5,180,418 | 1/1993 | Pissiotas et al. | 504/193 |
| 5,223,018 | 6/1993 | Moser | 504/221 |
| 5,393,735 | 2/1995 | Lange | 504/254 |

FOREIGN PATENT DOCUMENTS

| | | |
|---|---|---|
| 415 642 | 3/1991 | European Pat. Off. |
| 454 444 | 10/1991 | European Pat. Off. |
| 468 924 | 1/1992 | European Pat. Off. |
| WO87/07602 | 12/1987 | WIPO |

*Primary Examiner*—C. Warren Ivy
*Assistant Examiner*—D. Margaret M. Mach
*Attorney, Agent, or Firm*—Keil & Weinkauf

[57] ABSTRACT

Substituted N-phenylglutarimides I

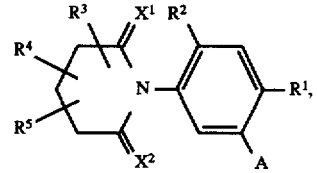

$X^1$, $X^2$=O, S; $R^1$=halogen, $NO_2$, CN, $CF_3$; $R^2$=H, halogen;

$R^3$, $R^4$, $R^5$=H, halogen, CN, alkyl, cycloalkyl, alkenyl, alkynyl, haloalkyl, alkoxy, haloalkoxy, alkylthio, haloalkylthio, cyanoalkyl, alkoxycarbonyl, unsubstituted or substituted phenyl or benzyl, or 2 substituents of a C atom or 2 substituents of adjacent C atoms of the glutarimide ring are bonded to one another via a chain which may be substituted;

$A=CHR^6$—$CHR^7$—CO—B or $CR^6$=$CR^8$—CO—B;

$R^6$=H, $C_1$–$C_6$-alkyl or $C_1$–$C_6$-haloalkyl;

$R^7$=halogen, haloalkyl, OH, alkoxy or alkylcarbonyloxy;

$R^8$=H, CN, alkyl, alkylcarbonyl, alkoxycarbonyl or

B=H, alkyl, alkenyl, alkynyl, haloalkyl, cycloalkyl, alkoxyalkyl, dialkoxyalkyl, alkylthioalkyl, alkoxy, alkylthio or amino, the last three radicals may be substituted, unsubstituted or functionalized;

and plant-tolerable salts of I;

their preparation and use as herbicides and desiccating/defoliating agents, and precursors for the preparation of the N-phenylglutarimides I.

13 Claims, No Drawings

SUBSTITUTED N-PHENYLGLUTARIMIDES AND N-PHENYLGLUTARAMIDES, THEIR PREPARATION AND USE

This application is a 371 of PCT/EP93/02879, filed Oct. 19, 1993.

DESCRIPTION

The present invention relates to novel substituted N-phenylglutarimides of the formula I

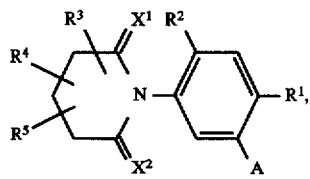

where the variables have the following meanings:

$X^1$, $X^2$
are oxygen or sulfur;
$R^1$
is halogen, nitro, cyano or trifluoromethyl;
$R^2$
is hydrogen or halogen;
$R^3$, $R^4$, $R^5$ independently of one another are hydrogen, halogen, cyano, $C_1$–$C_6$-alkyl, $C_3$–$C_7$-cycloalkyl, $C_2$–$C_6$-alkenyl, $C_2$–$C_6$-alkynyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-cyanoalkyl, $C_1$–$C_6$-alkoxycarbonyl, phenyl or benzyl, where the phenyl group or the phenyl ring of the benzyl group may be substituted by $C_1$–$C_6$-alkyl, $C_1$–$C_6$-alkoxy, halogen, cyano, nitro or trifluoromethyl, or two substituents of a carbon atom of the glutarimide ring are bonded to one another via a 2- to 5-membered chain and thus form a spiro ring, which, if desired, can carry one or two halogen atoms, the spiro ring in addition to the C atoms also being able to contain one or two non-adjacent ring members selected from the group consisting of —O—, —S—, —NH—, and —N($C_1$–$C_4$-alkyl)—, or two substituents of two adjacent carbon atoms of the glutarimide ring are bonded to one another via a 1- to 5-membered chain and thus form a fused ring, which, if desired, can carry one or two halogen atoms, the fused ring in addition to the C atoms also being able to contain one or two non-adjacent ring members selected from the group consisting of —O—, —S—, —NH— and —N($C_1$–$C_4$-alkyl)—;

A
is CHR$^6$—CHR$^7$—CO—B or CR$^6$=CR$^8$—CO—B, where $R^6$ is hydrogen, $C_1$–$C_6$-alkyl or $C_1$–$C_6$-haloalkyl;

$R^7$ is halogen, $C_1$–$C_6$-haloalkyl, hydroxyl, $C_1$–$C_6$-alkoxy or $C_1$–$C_6$-alkylcarbonyloxy, and $R^8$ is hydrogen, halogen, cyano, $C_1$–$C_6$-alkyl, $C_1$–$C_6$-haloalkyl, hydroxyl, $C_1$–$C_6$-alkoxy, $C_1$–$C_6$-alkylcarbonyl, $C_1$–$C_6$-alkoxycarbonyl or $C_1$–$C_6$-alkylcarbonyloxy and where
B has one of the following meanings:

(a) is hydrogen, (b) is $C_1$–$C_6$-alkyl, $C_3$–$C_6$-alkenyl, $C_3$–$C_6$-alkynyl, $C_1$–$C_6$-haloalkyl, $C_3$–$C_7$-cycloalkyl, $C_1$–$C_6$-alkoxy-$C_1$–$C_6$-alkyl, $C_1$–$C_6$-dialkoxy-$C_1$–$C_6$-alkyl or $C_1$–$C_6$-alkylthio-$C_1$–$C_6$-alkyl;

(c) is OR$^9$, SR$^9$, where $R^9$ is hydrogen, $C_1$–$C_6$-alkyl, $C_3$–$C_6$-alkenyl, $C_3$–$C_6$-alkynyl, $C_3$–$C_7$-cycloalkyl, halo-$C_1$–$C_6$-alkyl, $C_1$–$C_6$-cyanoalkyl, $C_3$–$C_6$-haloalkenyl, $C_1$–$C_6$-alkoxycarbonyl-$C_1$–$C_6$-alkyl, $C_1$–$C_6$-alkoxy-$C_1$–$C_6$-alkyl, $C_1$–$C_6$-alkylthio-$C_1$–$C_6$-alkyl, $C_1$–$C_6$-alkylimino or $C_1$–$C_6$-alkyloximino-$C_1$–$C_6$-alkyl, phenyl, phenyl substituted by one or more $C_1$–$C_6$-alkyl, $C_3$–$C_6$-alkenyl, halogen, cyano, nitro, $C_1$–$C_6$-alkoxy or $C_1$–$C_6$-alkoxycarbonyl radicals, benzyl or benzyl substituted by one or more $C_1$–$C_6$-alkyl, $C_3$–$C_6$-alkenyl, halogen, cyano, nitro, $C_1$–$C_6$-alkoxy or $C_1$–$C_6$-alkoxycarbonyl radicals;

(d) is NR$^{10}$R$^{11}$, where R$^{10}$ and R$^{11}$ independently of one another have the following meanings:

hydrogen, $C_1$–$C_6$-alkyl, $C_3$–$C_6$-alkenyl, $C_3$–$C_6$-alkynyl, $C_3$–$C_6$-cycloalkyl, $C_1$–$C_6$-haloalkyl, $C_1$–$C_6$-alkylcarbonyl, $C_1$–$C_6$-alkoxycarbonyl, $C_1$–$C_6$-alkoxy-$C_1$–$C_6$-alkyl, phenyl, phenyl substituted by one to three $C_1$–$C_6$-alkyl, $C_3$–$C_6$-alkenyl, halogen, cyano, nitro, $C_1$–$C_6$-alkoxy or $C_1$–$C_6$-alkoxycarbonyl radicals, or R$^{10}$ and R$^{11}$, together with the nitrogen atom to which they are bonded, are a saturated or unsaturated 4- to 7-membered heterocycle having one or two further identical or different heteroatoms selected from the group consisting of nitrogen, oxygen and sulfur;

and to the agriculturally utilizable salts of the substituted N-phenylglutarimides I.

In particular, the invention relates to substituted N-phenylglutarimides of the formula I where $R^3$ is $C_1$–$C_6$-alkyl or -haloalkyl and $R^4$, $R^5$ are hydrogen or $C_1$–$C_4$-alkyl and to glutarimides of the formula I′

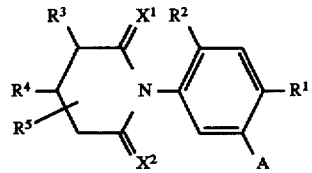

where $R^4$ is $C_1$–$C_6$-haloalkyl, $R^3$ and $R^5$ are hydrogen, $C_1$–$C_6$-alkyl or $C_1$–$C_6$-haloalkyl and A, $X^1$ and $X^2$ are as defined above.

Additionally, the invention relates to herbicidal and desiccant and/or defoliant compositions which contain these compounds as active substances.

A further aspect of the invention relates to N-phenylglutaramides of the general formula II

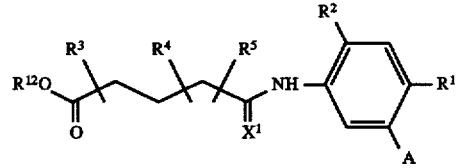

in which the variables $X^1$, $R^1$, $R^2$, $R^3$, $R^4$, $R^5$ and A have the same meaning as given above and $R^{12}$ is hydrogen, $C_1$–$C_6$-alkyl or benzyl.

The N-phenylglutaramides II are used as intermediates for preparing the substituted N-phenyl-glutarimides I, but can also be used as herbicides, bioregulators and agents for the abscission and/or defoliation of plant organs.

The Laid-Open Applications EP-A 391 847, EP-A 415 641, EP-A 415 642 and EP-A 454 444 disclose both herbicidally active, specifically substituted N-phenylglutarimides and specifically substituted N-phenylglutaramides. The Laid-Open Application WO 87/07 602 generally mentions N-phenyl-substituted glutarimides.

The efficiency and the selectivity of these known herbicides with respect to harmful plants is, however, only of limited satisfactoriness, so the invention is based on the object of novel herbicidally active compounds with which harmful plants can be combated better and more specifically than previously and which are well tolerated by the crop plants.

Accordingly, the substituted N-phenylglutarimides I and the N-phenylglutaramides II defined at the beginning have been found.

In addition, agents have been found which contain these substances and have a good herbicidal action.

Additionally, it has been found that the compounds I and II according to the invention are suitable as defoliating and desiccating agents, for example in cotton, potato, rape, sunflowers, soybeans or field beans.

The meanings mentioned for the substituents $R^1$ to $R^5$ are collective terms for individual lists of the individual group members. All alkyl, alkenyl, alkynyl and haloalkyl moieties can be straight-chain or branched. The haloalkyl and haloalkoxy radicals can carry identical or different halogen atoms.

The substituents have the following specific meanings, for example:

$X^1$, $X^2$
are oxygen or sulfur, preferably $X^1$ and $X^2$ are both oxygen or $X^1$ is sulfur and $X^2$ is oxygen;

$R^1$
is nitro, cyano, trifluoromethyl or halogen, such as fluorine, chlorine, bromine or iodine, preferably halogen, in particular chlorine;

$R^2$
is hydrogen or halogen such as given for $R^1$, preferably hydrogen, chlorine or fluorine;

$R^3$, $R^4$, $R^5$ independently of one another
are hydrogen, halogen as mentioned for $R^1$, cyano, $C_1$–$C_6$-alkyl, in particular $C_1$–$C_4$-alkyl: methyl, ethyl, n-propyl, isopropyl, n-butyl, sec-butyl, tert-butyl, $C_3$–$C_7$-cycloalkyl: cyclopropyl, cyclobutyl, cyclopentyl, cyclohexyl and cycloheptyl, $C_2$–$C_6$-alkenyl or $C_2$–$C_6$-alkynyl, in particular $C_2$–$C_4$-alkenyl or -alkynyl: eg. vinyl, allyl, ethynyl, propargyl, $C_1$–$C_6$-haloalkyl: chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 3-chloropropyl, preferably trifluoromethyl, $C_1$–$C_6$-alkoxy and -haloalkoxy, in particular $C_1$–$C_4$-alkoxy and $C_1$–$C_4$-haloalkoxy: eg. methoxy, ethoxy, n-propoxy, 1-methylethoxy, n-butoxy, 1-methylpropoxy, 2-methylpropoxy, 1,1-dimethylethoxy, n-pentoxy, 1-methylbutoxy, 2-methylbutoxy, 3-methylbutoxy, chloromethoxy, dichloromethoxy, trichloromethoxy, fluoromethoxy, difluoromethoxy, trifluoromethoxy, chlorofluoromethoxy, dichlorofluoromethyloxy, chlorodifluoromethyloxy, 1-fluoroethyloxy, 2-fluoroethyloxy, 2,2-difluoroethyloxy, 2,2,2-trifluoroethyloxy, 2-chloro-2-fluoroethyloxy, 2-chloro-2,2-difluoroethyloxy, 2,2-dichloro-2-fluoroethyloxy, 2,2,2-trichloroethyloxy and pentafluoroethyloxy, preferably $C_1$–$C_2$-alkoxy or $C_1$–$C_2$-haloalkoxy such as 2,2,2-trifluoroethoxy or methoxy, $C_1$–$C_6$-, in particular $C_1$–$C_4$-alkylthio and $C_1$–$C_4$-haloalkylthio: eg. methylthio, ethylthio, n-propylthio, 1-methylethylthio, n-butylthio, 1-methylpropylthio, 2-methylpropylthio, 1,1-dimethylethylthio, 2-methylpropylthio, 1,1-dimethylethylthio, chloromethylthio, dichloromethylthio, trifluoromethylthio, fluoromethylthio, difluoromethylthio, trifluoromethylthio, 2,2,2-trifluoroethylthio and pentafluoroethylthio, $C_1$–$C_6$-, in particular $C_1$–$C_4$-cyanoalkyl: eg. cyanomethyl, 1-cyanoeth-1-yl and 2-cyanoeth-1-yl, $C_1$–$C_6$-alkoxycarbonyl, in particular $C_1$–$C_4$-alkoxycarbonyl, where the radicals mentioned above for $C_1$–$C_4$-alkoxy are also preferred in the combination alkoxycarbonyl: particularly preferably methoxy- and ethoxycarbonyl, phenyl or benzyl, where the aromatic nucleus can in each case be substituted by one or more radicals, in particular 1 to 3 radicals, selected from the group consisting of $C_1$–$C_6$-alkyl, $C_1$–$C_6$-alkoxy, in particular methyl, ethyl, ethoxy or methoxy, halogen such as fluorine, chlorine, bromine or iodine, cyano, nitro and trifluoromethyl; for example phenyl, 4-fluorophenyl, 4-chlorophenyl, 3-fluorophenyl, 3-chlorophenyl, 2-fluorophenyl, 2-chlorophenyl, 2,4-dichlorophenyl, 4-trifluoromethylphenyl, 4-methoxyphenyl, benzyl or 2,4-dichlorobenzyl.

Two geminally bonded radicals ($R^3+R^4$ or $R^4+R^5$) can also form a 2- to 5-membered chain, (eg. an ethylene, propylene, butylene or pentylene chain), with one another and thus form a spiro-fused ring with one another, which can be unsubstituted or in turn can carry 1 or 2 halogen atoms such as fluorine, chlorine or bromine;

two vicinally bonded radicals ($R^3+R^4$ or $R^4+R^5$) can also form a 1- to 5-membered chain (eg. a methylene, ethylene, propylene, butylene or pentylene chain), with one another and thus form, together with the C atoms to which they are bonded, a fused 3- to 7-membered carbocyclic ring, which can be unsubstituted or in turn can carry 1 or 2 halogen atoms such as fluorine, chlorine, bromine or iodine;

both the spiro ring and the fused ring, in addition to the C atoms as ring members, can also contain one or two non-adjacent ring members, to be specific —O—, —S—, —NH— or —N($C_1$–$C_4$-alkyl)— in each case.

A is a group $$-CHR^6-CHR^7-\overset{O}{\underset{\|}{C}}-B \quad \text{or} \quad -CR^6=CR^8-\overset{O}{\underset{\|}{C}}-B$$

where $R^6$ in each case is hydrogen, $C_1$–$C_6$-alkyl, in particular $C_1$–$C_4$-alkyl such as methyl, ethyl, n-propyl, isopropyl, n-butyl, sec-butyl, tert-butyl, in particular methyl and ethyl, $C_1$–$C_6$-, in particular $C_1$- and $C_2$-haloalkyl such as chloromethyl, dichloromethyl, tri-chloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 3-chloropropyl, preferably trifluoromethyl and $R^7$ is halogen such as fluorine, chlorine, bromine or iodine, in particular chlorine and bromine, is $C_1$–$C_6$-haloalkyl as mentioned above for $R^6$, in particular trifluoromethyl and pentafluoromethyl, is hydroxyl, is $C_1$–$C_6$-alkoxy or $C_1$–$C_6$-alkylcarbonyloxy, where in both groups the alkyl radicals preferably have 1 to 4 C atoms, such as methyl, ethyl, n-propyl, isopropyl, n-butyl, isobutyl, sec-butyl, tert-butyl, ie. for example methoxy, ethoxy, methoxycarbonyl and ethoxycarbonyl.

$R^8$ is preferably hydrogen, cyano, hydroxyl, halogen such as fluorine, chlorine, bromine or iodine, in particular chlorine or bromine, $C_1$–$C_6$-, in particular $C_1$–$C_4$-alkyl such as methyl, ethyl, n-propyl, isopropyl, n-butyl, isobutyl, sec-butyl, tert-butyl, $C_1$–$C_6$-haloalkyl, in particular $C_1$–$C_4$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 3-chloropropyl, particularly preferably trifluoromethyl or alkoxy, alkylcarbonyl, alkoxycarbonyl or alkylcarbonyloxy, where the alkyl units in the four last-mentioned groups have 1 to 6, preferably 1 to 4, C atoms such as methyl, ethyl, n-propyl, isopropyl, n-butyl, isobutyl, sec-butyl, tert-butyl, ie. for example methoxy, ethoxy, methylcarbonyl, ethylcarbonyl, methoxycarbonyl, ethoxycarbonyl, isopropoxycarbonyl, methylcarbonyloxy or ethylcarbonyloxy.

The radical B is very broadly variable and is (a) hydrogen;

(b) $C_1$–$C_6$-, in particular $C_1$–$C_4$-alkyl such as methyl, ethyl, n-propyl, isopropyl, n-butyl, isobutyl, sec-butyl, tert-butyl; $C_3$–$C_6$-alkenyl or $C_3$–$C_6$-alkynyl, such as allyl or propargyl; $C_1$–$C_6$-, in particular $C_1$–$C_2$-haloalkyl such as trifluoromethyl, 2,2,2-trifluoroethyl or 2,2,2-trichloroethyl; $C_3$–$C_7$-cycloalkyl, in particular $C_3$–$C_6$-cycloalkyl such as cyclopropyl, cyclopentyl or cyclohexyl; $C_1$–$C_6$-alkoxy- or -dialkoxy-$C_1$–$C_6$-alkyl, in particular $C_1$–$C_4$-alkoxy- or -dialkoxy-$C_1$–$C_4$-alkyl such as methoxymethyl, ethoxymethyl, dimethoxymethyl, diethoxymethyl or i-propoxymethyl; $C_1$–$C_6$-alkylthio-$C_1$–$C_6$-alkyl, in particular $C_1$–$C_4$-alkylthio-$C_1$–$C_6$-alkyl, eg. methylthiomethyl or ethylthiomethyl, (c) $OR^9$, $SR^9$, where $R^9$ has the following meanings: hydrogen, $C_1$–$C_6$-, in particular $C_1$–$C_4$-alkyl as mentioned above for (b), $C_3$–$C_6$-alkenyl and -alkynyl, eg. allyl or propargyl; $C_3$–$C_7$-cycloalkyl, eg. cyclopropyl, cyclopentyl or cyclohexyl, $C_1$–$C_6$-haloalkyl such as 2,2,2-trifluoromethyl or 2,2,2-trichloroethyl; $C_1$–$C_6$-, in particular $C_1$–$C_4$-cyanoalkyl, eg. cyanomethyl, 2-cyanoethyl or 1-cyanoethyl; $C_3$–$C_6$-haloalkenyl, in particular $C_3$- and $C_4$-fluoro- or chloroalkenyl, eg. 3-chloroallyl or 2,3-dichloroallyl; $C_1$–$C_6$-alkoxycarbonyl-$C_1$–$C_6$-alkyl, in particular $C_1$–$C_4$-alkoxycarbonyl-$C_1$–$C_6$-alkyl such as methoxycarbonylmethyl, ethoxycarbonylmethyl, methoxycarbonylethyl or ethoxycarbonylethyl, $C_1$–$C_6$-alkoxy- or $C_1$–$C_6$-alkylthio-$C_1$–$C_6$-alkyl, in particular $C_1$–$C_4$-alkoxy-$C_1$–$C_4$-alkyl or $C_1$–$C_4$-alkylthio-$C_1$–$C_4$-alkyl, eg. methoxymethyl, ethoxymethyl, methoxyethyl or ethoxyethyl and the corresponding alkylthio-alkyl radicals; $C_1$–$C_6$-alkylimino, in particular $C_1$–$C_4$-alkylimino, eg. ethylimino or 2-propylimino; $C_1$–$C_6$-alkyloximino-$C_1$–$C_6$-alkyl, in particular $C_1$–$C_4$-alkyloximino-$C_1$–$C_4$-alkyl, eg. 2-propyloximinoethyl or 2-propyloximinopropyl;

phenyl or phenyl which is substituted by one or more radicals, in particular one to three radicals, selected from the group consisting of $C_1$–$C_6$-alkyl, in particular methyl, ethyl, propyl; $C_3$–$C_6$-alkenyl, eg. allyl, halogen, eg. fluorine, chlorine, bromine or iodine, cyano, nitro; $C_1$–$C_6$-alkoxy, eg. methoxy or ethoxy or $C_1$–$C_6$-alkoxycarbonyl, in particular $C_1$–$C_4$-alkoxycarbonyl, eg. methoxycarbonyl, and benzyl or benzyl which is substituted on the phenyl group as defined above;

(d) $NR^{10}R^{11}$, where $R^{10}$ and $R^{11}$ have the following meanings:

hydrogen, $C_1$–$C_6$-alkyl, in particular $C_1$–$C_4$-alkyl such as methyl, ethyl, n-propyl, isopropyl, n-buryl, isobutyl, tert-butyl, sec-butyl; $C_3$–$C_6$-alkenyl or $C_3$–$C_6$-alkynyl, eg. allyl, propargyl; $C_3$–$C_7$-cycloalkyl such as cyclopropyl, cyclopentyl and cyclohexyl; $C_1$–$C_6$-haloalkyl, in particular $C_1$–$C_4$-haloalkyl, where halogen is preferably fluorine, chlorine or bromine, eg. 2,2,2-trifluoroethyl; $C_1$–$C_6$-alkylcarbonyl or $C_1$–$C_6$-alkoxycarbonyl, in particular $C_1$–$C_4$-alkylcarbonyl or $C_1$–$C_4$-alkoxycarbonyl such as methoxycarbonyl, ethoxycarbonyl, methylcarbonyl or ethylcarbonyl; $C_1$–$C_6$-alkoxy-$C_1$–$C_6$-alkyl, in particular $C_1$–$C_4$-alkoxy-$C_1$–$C_4$-alkyl, eg. methoxymethyl, ethoxymethyl, n-propoxymethyl, tert-butoxymethyl, 1-methoxyethyl, 2-methoxyethyl, 2-ethoxypropyl; phenyl, phenyl substituted by 1 to 3 radicals selected from the group consisting of $C_1$–$C_6$-alkyl, in particular methyl, ethyl, $C_3$–$C_6$-alkenyl, eg. alkyl; halogen such as fluorine, chlorine, bromine or iodine, cyano, nitro, $C_1$–$C_6$-alkoxy or -alkoxycarbonyl, in particular $C_1$–$C_4$-alkoxy or $C_1$–$C_4$-alkoxycarbonyl, eg. methoxy or ethoxy, methoxycarbonyl or ethoxycarbonyl;

$R^{10}$ and $R^{11}$ can also form, together with the nitrogen atom to which they are bonded, a saturated or unsaturated 4- to 7-membered heterocycle, in particular 6-membered heterocycle, in which a ring member is —NH—, —S— or —O—; for example $R^{10}$ and $R^{11}$ together form a group —$CH_2$—$CH_2$—O—$CH_2$—$CH_2$, $CH_2$—$CH_2$—S— $CH_2$—$CH_2$, $CH_2$—$CH_2$—O—$CH$=$CH$—.

With respect to the use of the substituted N-phenylglutarimides I and the N-phenylglutaramide derivatives II according to the invention as herbicidally active compounds and compounds having defoliant/desiccant activity, the following meanings of the variable B are very particularly preferred:

TABLE 1

| No. | B | No. | B |
| --- | --- | --- | --- |
| B.01 | —H | B.39 | —O—($CH_3$-phenyl) |
| B.02 | —OH | B.40 | —O—(2,4-$Cl_2$-phenyl) |
| B.03 | —$OCH_3$ | B.41 | —O—(2,4-($CH_3$)$_2$-phenyl-) |
| B.04 | —$OC_2H_5$ | B.42 | —O—$CH_2CN$ |
| B.05 | —O-n-$C_3H_7$ | B.43 | —O—$CH_2CH$=$CCl_2$ |
| B.06 | —O-i-$C_3H_7$ | B.44 | —O—$CH_2CH$=$CHCl$ |
| B.07 | —O-n-$C_4H_9$ | B.45 | —O—$CH_2OCH_3$ |
| B.08 | —O-i-$C_4H_9$ | B.46 | —O—$CH_2OC_2H_5$ |

TABLE 1-continued

| No. | B | No. | B |
|---|---|---|---|
| B.09 | —O-s-$C_4H_9$ | B.47 | —O—$C_2H_4OCH_3$ |
| B.10 | —O-tert.-$C_4H_9$ | B.48 | —O—$C_2H_4OC_2H_5$ |
| B.11 | —O-n-$C_5H_{11}$ | B.49 | —O—$CH(CH_3)$—$OCH_3$ |
| B.12 | —O-n-$C_6H_{13}$ | B.50 | —O—$CH(CH_3)$—$OC_2H_5$ |
| B.13 | —O—$CH_2CH=CH_2$ | B.51 | —$OCH_2C=NOCH_3$ |
| B.14 | —O—$CH(CH_3)CH=CH_2$ | B.52 | —O—$C_2H_4C=NOCH_3$ |
| B.15 | —O—CH—CH=CH—$CH_2$ | B.53 | —O—$CH_2C=NOC_2H_5$ |
| B.16 | —O—$CH_2$—C≡CH | B.54 | —O—$C(O)CH_3$ |
| B.17 | —O—$CH(CH_3)$—C≡CH | B.55 | —O—$C(O)C_2H_5$ |
| B.18 | —O—$CH_2$—C≡C—$CH_3$ | B.56 | —O—$C_2H_4C=NOC_2H_5$ |
| B.19 | —O-cyclopropyl | B.57 | —$SCH_3$ |
| B.20 | —O-cyclobutyl | B.58 | —$SC_2H_5$ |
| B.21 | —O-cyclopentyl | B.59 | —S-n-$C_3H_7$ |
| B.22 | —O-cyclohexyl | B.60 | —S-i-$C_3H_7$ |
| B.23 | —O—$CH_2$—$CF_3$ | B.61 | —S—$CH_2CH=CH_2$ |
| B.24 | —O—$CH_2$—$CCl_3$ | B.62 | —S—$CH_2C≡CH$ |
| B.25 | —O—$(CH_2)_3$—Br | B.63 | —S-phenyl |
| B.26 | —O-phenyl | B.64 | —S—$CH_2CN$ |
| B.27 | —O-(2-F-phenyl) | B.65 | —S—$CH_2OCH_3$ |
| B.28 | —O-(2-Cl-phenyl) | B.66 | —$CH_3$ |
| B.29 | —O-(2-Br-phenyl) | B.67 | —$C_2H_7$ |
| B.30 | —O-(3-F-phenyl) | B.68 | -n-$C_3H_7$ |
| B.31 | —O-(3-Cl-phenyl) | B.69 | -i-$C_3H_7$ |
| B.32 | —O-(3-Br-phenyl) | B.70 | -n-$C_4H_9$ |
| B.33 | —O-(4-F-phenyl) | B.71 | -i-$C_4H_9$ |
| B.34 | —O-(4-Cl-phenyl) | B.72 | -s-$C_4H_9$ |
| B.35 | —O-(4-Br-phenyl) | B.73 | -tert.-$C_4H_9$ |
| B.36 | —O-(4-$OCH_3$-phenyl) | B.74 | -n-$C_5H_{11}$ |
| B.37 | —O-(4-CN-phenyl) | B.75 | -n-$C_6H_{13}$ |
| B.38 | —O-(4-$COOCH_3$-phenyl) | B.76 | —$CH_2CH=CH_2$ |
| B.77 | —$CH_2C≡CH$ | B.108 | —NH—$CH(CH_3)$—CH=$CH_2$ |
| B.78 | —$CH(CH_3)CH=CH_2$ | B.109 | —NH—$CH_2$—C≡CH |
| B.79 | —$CH(CH_3C≡CH)$ | B.110 | —NH—$CH(CH_3)$—C≡CH |
| B.80 | —$CH_2Cl$ | B.111 | —$N(CH_3)$—$CH_2CH=CH$ |
| B.81 | —$CH_2Br$ | B.112 | —$N(CH_3)$—$CH_2C≡CH$ |
| B.82 | —$CHCl_2$ | B.113 | —NH-cyclopropyl |
| B.83 | —$CF_3$ | B.114 | —NH-cyclobutyl |
| B.84 | -Cyclopropyl | B.115 | —NH-cyclopentyl |
| B.85 | -Cyclobutyl | B.116 | —NH-cyclohexyl |
| B.86 | -Cyclopentyl | B.117 | —$N(CH_3)$-cyclohexyl |
| B.87 | -Cyclohexyl | B.118 | —$N(C_2H_5)$-cyclohexyl |
| B.88 | -Phenyl | B.119 | —NH—$COCH_3$ |
| B.89 | 2-F-phenyl | B.120 | —NH—$COC_2H_5$ |
| B.90 | 3-F-phenyl | B.121 | —NH—$COOCH_3$ |
| B.91 | 4-F-phenyl | B.122 | —NH—$CH_2OCH_3$ |
| B.92 | 2-Cl-phenyl | B.123 | —NH—$(CH_2)_2CCH_3$ |
| B.93 | 4-Cl-phenyl | B.124 | —N-piperindinyl |
| B.94 | 2,4-$Cl_2$-phenyl | B.125 | —N-pyrrolidinyl |
| B.95 | —$CH_2$—$OCH_3$ | B.126 | —N-morpholin-4-yl |
| B.96 | —$CH(OCH_3)_2$ | B.127 | —N-piperazinyl |
| B.97 | —$CH_2$—$SCH_3$ | B.128 | —NH-phenyl |
| B.98 | —$NH_2$ | B.129 | —NH—(2-$CH_3$-phenyl) |
| B.99 | —$NHCH_3$ | B.130 | —NH-(2-F-phenyl) |
| B.100 | —NH-n-$C_3H_7$ | B.131 | —NH-(4-F-phenyl) |
| B.101 | —NH-i-$C_3H_7$ | B.132 | —NH-(2-Cl-phenyl) |
| B.102 | —NH-n-$C_4H_9$ | B.133 | —NH-(4-Cl-phenyl) |
| B.103 | —$N(CH_3)_2$ | B.134 | —NH-(2,4-$Cl_2$-phenyl) |
| B.104 | —$N(C_2H_5)_2$ | B.135 | —O—CO—$OCH_3$ |
| B.105 | —$N(CH_3)C_2H_5$ | B.136 | —O—CO—$OC_2H_5$ |
| B.106 | —$N(n-C_3H_7)_2$ | B.137 | —O—$CH_2$—$COOCH_3$ |
| B.107 | —NH—$CH_2CH=CH_2$ | B.138 | —O—$CH(CH_3)$—$COOCH_3$ |

The compounds of the formula I can be present in the form of their agriculturally utilizable salts, the nature of the salt in general not being a problem. Customarily the salts of those bases are suitable which do not adversely affect the herbicidal action of I.

Suitable salts are for example alkali metal salts, in particular sodium and potassium salts, alkaline earth metal salts such as, in particular, calcium, magnesium and barium salts, manganese, copper, zinc or iron salts and also ammonium salts such as tetraalkyl- and benzyltrialkylammonium salts, phosphonium salts, sulfonium salts such as trialkylsulfonium salts or sulfoxonium salts.

The substituted N-phenylglutarimides of the formula I are obtainable by various routes, to be precise preferably by one of the following processes:

a) where $X^1$=O, S and $X^2$=O, by cyclizing an N-phenylglutaramide of the formula II

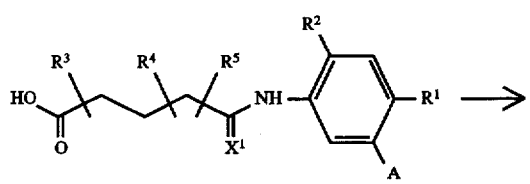

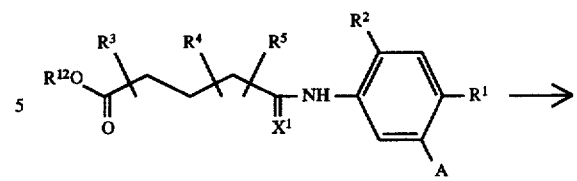

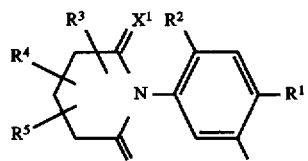

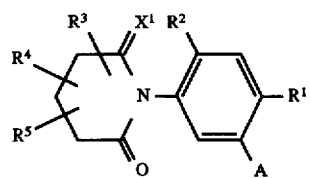

The reaction is customarily carried out in an inert solvent and in the presence of a dehydrating agent.

The solvents used are inert organic solvents such as hydrocarbons, eg. n-hexane, ligroin or petroleum ether; aromatics, eg. toluene or xylene, halogenated hydrocarbons, eg. dichloromethane, trichloromethane or chlorobenzene; ethers, eg. 1,2-dimethoxyethane, diethyl ether, tetrahydrofuran or dioxane; ketones such as acetone and tert-butyl methyl ketone; alcohols such as methanol, ethanol and isopropanol; nitriles such as acetonitrile; polar organic solvents such as dimethylformamide and dimethyl sulfoxide; organic acids, eg. acetic acid or trifluoroacetic acid; water or mixtures of these.

Possible dehydrating reagents are eg. acid halides, eg. acetyl chloride, propionyl chloride, thionyl chloride, phosphorus oxychloride or phosphorus pentachloride; anhydrides, such as acetic anhydride, or acids, eg. phosphoric acid, polyphosphoric acid or sulfuric acid.

The ratio of dehydrating agent/starting material II is not critical. Customarily, from 0.5 to 1.5 equivalents, preferably from 0.7 to 1.2 equivalents, are used. In some cases, however, it may be useful to use the dehydrating agent in a large excess and thus simultaneously as a solvent.

The reaction temperature is between approximately 0° C. and 150° C., preferably between 35° C. and the reflux temperature of the solvent used.

In some cases, it may be advantageous to remove the water formed in the reaction from the reaction by physical means, such as eg. azeotropic distillation, water removal or dehydration by means of molecular sieve, so that in some cases a chemical dehydrating agent can be dispensed with.

Normally the reaction is carried out at atmospheric pressure or under the autogenous pressure of the respective solvent. A higher or lower pressure is possible, but in general offers no advantages.

b) where $X^1$=O, S and $X^2$=O, by cyclizing an N-phenylglutaramide of the formula II in an inert solvent and in the presence of an acid or a base.

Suitable solvents are hydrocarbons, eg. n-hexane, ligroin or petroleum ether; aromatics such as toluene and xylene; halogenated hydrocarbons, eg. dichloromethane, trichloromethane or chlorobenzene; organic nitrogen bases, eg. triethylamine or pyridine; ethers such as 1,2-dimethoxyethane, diethyl ether, tetrahydrofuran and dioxane; ketones such as acetone and tert-butyl methyl ketone; alcohols such as methanol, ethanol and isopropanol; nitriles such as acetonitrile; polar organic solvents, eg. dimethylformamide, N-methylpyrrolidone or dimethyl sulfoxide; organic acids, eg. acetic acid or trifluoroacetic acid; water or mixtures of these solvents.

The bases customarily used are organic nitrogen bases, eg. pyridine, triethylamine or 1,4-diazabicyclo[2.2.2]octane; or inorganic bases, eg. sodium hydride, sodium hydroxide, potassium hydroxide, sodium carbonate or potassium carbonate; alkali metal alkoxides such as sodium methoxide, sodium ethoxide and potassium tert-butoxide.

Suitable acids are eg. organic acids such as p-toluenesulfonic acid and acetic acid, or mineral acids such as sulfuric acid and phosphoric acid, it being possible to use the acids at the same time also as solvents or diluents.

The reaction temperature is between 20° C. and 200° C., preferably between 50° C. and the reflux temperature of the solvent used.

The details for method a) apply with respect to the pressure.

c) where $X^1$=S and $X^2$=O or S, by reacting a substituted N-phenylglutarimide of the formula I, where $X^1$ is oxygen, with a suitable sulfurizing reagent

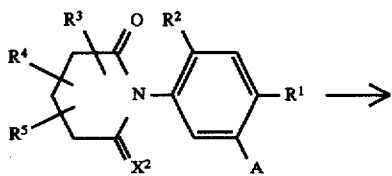

-continued

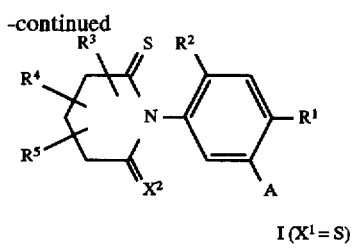

I (X¹ = S)

As a rule, the reaction is carried out in an inert solvent. Possible solvents are eg. aromatics, such as toluene or xylene, chlorinated hydrocarbons, eg. dichloromethane, chloroform or chlorobenzene; ethers such as dialkyl ethers, 1,2-dimethoxyethane, tetrahydrofuran and dioxane; alcohols such as methanol and ethanol; ketones such as acetone, or water, and also a mixture of these solvents.

Particularly useful sulfurizing reagents are phosphorus (V) sulfide and 2,4-bis-(4-methoxyphenyl)-1,2,3,4-dithiadiphosphetane-2,4-dithione ("Lawesson's Reagent").

The amount of sulfurizing reagent is not critical, normally 1 to 5 times the molar amount is used, based on the N-phenyl-substituted glutarimide to be sulfurized, if it is wished to replace both groups $X^1$ and $X^2$=O by sulfur. If it is desired to replace only one radical X, then approximately equimolar amounts are advantageously selected.

Normally, the reaction temperature is between 20° C. and 200° C., preferably between 40° C. and the reflux temperature of the solvent used.

If the glutarimide of the formula 1 to be sulfurized has another carbonyl group which is more reactive to the sulfurizing reagent than the imide group, eg. if B is hydrogen or alkyl, then the selectivity of the sulfurizing reaction can be guaranteed by a protective group technique by blocking, for example, the carbonyl group in the side chain A by a customary protective group. Useful protective groups are eg. acetals or other groups which are well-known to the person skilled in the art, such as are described eg. in "Protective Groups in Organic Synthesis", Th. W. Greene, Wiley & Sons, New York, 1981.

In general, the substituted N-phenylglutarimides I can be prepared by one of the abovementioned synthesis processes. For economical or process engineering reasons, however, it may be more expedient to prepare some compounds I from similar substituted N-phenylglutarimides I which differ, however, in particular in the meaning of the radicals A or B, to be precise in a manner known per se, eg. by ester hydrolysis, esterification, amidation, acetalization, acetal hydrolysis, condensation reaction, Wittig reaction, Peterson olefination, etherification, alkylation, oxidation or reduction.

The substituted N-phenylglutarimides I may be obtained in the processes described above as isomer mixtures. However, the isomers obtained can be separated into the pure isomers, if desired, using the methods customary for this purpose, eg. by crystallization, chromatography (LC, HPLC, etc.), if appropriate on an optically active adsorbate.

The N-phenylglutaramides of the formula II are novel. They are useful intermediate compounds for preparing the final products of the formula I according to the invention. The invention thus also relates to novel glutaramides or glutaric ester amides (formula II), in which the radicals $R^1$ to $R^8$, $X^1$, $X^2$, A and B are defined as under formula I and the radical $R^9$ is H, $C_1$–$C_6$-alkyl or benzyl.

The compounds II surprisingly additionally also show herbicidal activity and defoliant/desiccant action.

The N-phenylglutaramides II are obtainable by various routes, to be precise preferably by one of the following processes:

d) by reacting an aniline of the formula III with a glutaric anhydride of the formula IV

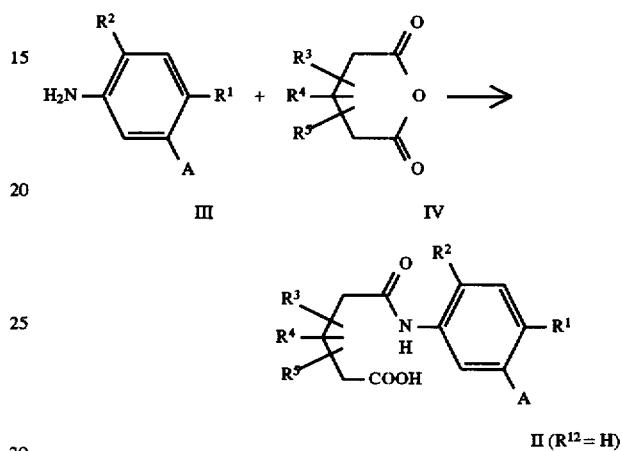

II ($R^{12}$ = H)

Suitable solvents for this reaction are eg. ethers such as diethyl ether, tetrahydrofuran and dioxane; hydrocarbons such as hexane, petroleum ether, toluene and xylene; acetonitrile; amides such as dimethylformamide and chlorinated hydrocarbons such as dichloromethane, chloroform and chlorobenzene, as well as mixtures of the solvents mentioned.

The reaction is customarily carried out in a temperature range from −20° to 100° C., preferably 0° to 70° C.

The reaction is expediently carried out at atmospheric pressure or under the autogenous pressure of the particular solvent. A higher or lower pressure is possible, but in general offers no advantages.

e) By reacting an aniline of the formula III with a glutaric acid monoester of the formula V in the presence of a base.

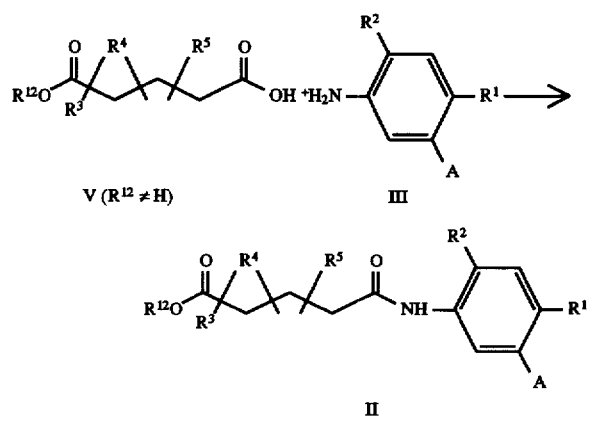

Useful solvents for this reaction are eg. hydrocarbons such as hexane, petroleum ether, benzene, toluene and xylene; halogenated hydrocarbons such as dichloromethane, chloroform, carbon, tetrachloride and chlorobenzene; ethers such as diethyl ether, tert-butyl methyl ether, tetrahydrofuran and dioxane; ketones such as acetone; nitriles such as acetonitrile; tertiary amines, such as pyridine or N,N-diethylaniline; acid amides such as dimethylformamide and N-methylpyrrolidone; organic sulfur compounds such as dimethyl sulfoxide and sulfolane; and further water or mixtures of these solvents.

Useful bases are eg. organic nitrogen bases such as pyridine, triethylamine and 1,4-diazabicyclo[2.2.2]-octane, inorganic bases such as sodium hydride, potassium hydride, potassium hydroxide, sodium hydroxide, sodium carbonate and potassium carbonate; metal alkoxides such as sodium methoxide, sodium ethoxide and potassium tert-butoxide.

The ratio of the base to III is customarily from 0.5 to 1.5, preferably from 0.7 to 1.2.

In a preferred embodiment, the acid V is converted before reaction with III into an activated acid derivative for example a halide, preferably chloride, an imidazolide or a mixed anhydride, eg. with ethylcarbonic acid. Suitable reagents for this purpose are eg. thionyl chloride, phosphorus oxychloride, phosgene or imidazole or ethyl chloroformate.

In some cases, a condensation reagent, eg. dicyclohexylcarbodiimide, can also be used instead of a base.

The reaction temperature is between −40° and 160° C., preferably −20° and 130° C.

The ratio of the starting compounds III and IV is not critical; preferably approximately equimolar amounts of both starting materials are reacted.

The details for method d) apply with respect to the pressure.

f) By reacting a compound of the formula II, where $X^1$ is oxygen, with a suitable sulfurizing reagent

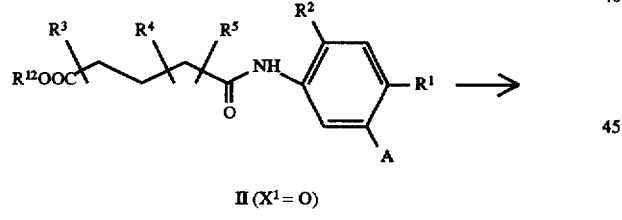

II ($X^1$ = O)

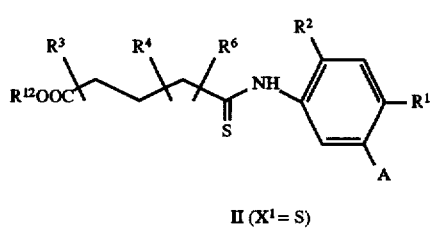

II ($X^1$ = S)

The reaction conditions, solvent etc. are already described above for I (process c) and can be applied analogously to II.

The details for method d) apply with respect to the pressure.

Another manner of preparation of the substituted N-phenylglutarimides I according to the invention is direct preparation from the aniline III without isolation of the intermediates II.

The starting materials III, IV and V are known or can be prepared by processes known per se, eg. as described in EP-A-391 847, 415 642, 454 444, DE-A-3 941 562, DE-A-40 42 194, EP-A-400 427 or EP-A-415 641.

Among the substituted N-phenylglutarimides, the compounds I'

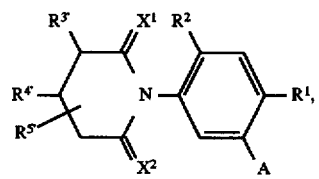

where $R^{4'}$ is $C_1$-$C_6$-haloalkyl, $R^{3'}$ and $R^{5'}$ independently of one another are hydrogen, $C_1$-$C_6$-alkyl or $C_1$-$C_6$-haloalkyl, are particularly preferred.

With respect to herbicidal use, very particularly preferred compounds I' are shown in the following table 2.

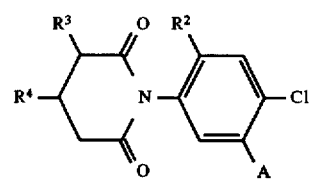

Where $R^2$ = H
$R^3$ = H
$R^4$ = CF$_3$

TABLE 2

| No. | A |
|---|---|
| Ia1 | CH$_2$—CHCl—COOCH$_3$ |
| Ia2 | CH$_2$—CHCl—COOC$_2$H$_5$ |
| Ia3 | CH$_2$—CHBr—COOCH$_3$ |
| Ia4 | CH$_2$—CHBr—COOC$_2$H$_5$ |
| Ia5 | CH$_2$—CHI—COOCH$_3$ |
| Ia6 | CH$_2$—CHI—COOC$_2$H$_5$ |
| Ia7 | CH=CH—COOCH$_3$ |
| Ia8 | CH=CH—COOC$_2$H$_5$ |
| Ia9 | CH=CCl—COOCH$_3$ |
| Ia10 | CH=CCl—COOC$_2$H$_5$ |
| Ia11 | CH=CBr—COOCH$_3$ |
| Ia12 | CH=CBr—COOC$_2$H$_5$ |
| Ia13 | CH=CI—COOCH$_3$ |
| Ia14 | CH=CI—COOC$_2$H$_5$ |
| Ia15 | CH=CF—COOCH$_3$ |
| Ia16 | CH=CF—COOC$_2$H$_5$ |
| Ia17 | CH=C(CN)—COOCH$_3$ |
| Ia18 | CH=C(CN)—COOC$_2$H$_5$ |
| Ia19 | CH=C(COOCH$_3$)$_2$ |
| Ia20 | CH=C(COOC$_2$H$_5$)$_2$ |
| Ia21 | CH=C(COOCH$_3$)—COOC$_2$H$_5$ |
| Ia22 | CH=C(CH$_3$)—COOCH$_3$ |
| Ia23 | CH=C(CH$_3$)—COOC$_2$H$_5$ |
| Ia24 | CH=C(C$_2$H$_5$)—COOC$_2$H$_5$ |
| Ia25 | CH=C(CF$_3$)—COOCH$_3$ |
| Ia26 | CH=C(CF$_3$)—COOC$_2$H$_5$ |
| Ia27 | CH=C(COCH$_3$)—COOCH$_3$ |
| Ia28 | CH=C(COCH$_3$)—COOC$_2$H$_5$ |
| Ia29 | CH=CH—CO—CH$_3$ |
| Ia30 | CH=CH—CO—CH$_2$Cl |
| Ia31 | CH=CH—CO—CHCl$_2$ |
| Ia32 | CH=CH—CO—CH$_2$OCH$_3$ |
| Ia33 | CH=CCl—COCH$_3$ |
| Ia34 | CH=CBr—COCH$_3$ |
| Ia35 | CH=C(CH$_3$)—CHO |
| Ia36 | CH=C(CH$_3$)—CO—CH$_3$ |
| Ia37 | CH=CH—COO(CH$_2$)$_2$OCH$_3$ |

TABLE 2-continued

| No. | A |
|---|---|
| Ia38 | CH=CH—COO(CH₂)₂OC₂H₅ |
| Ia39 | CH=CCl—COO(CH₂)₂OCH₃ |
| Ia40 | CH=CCl—COO(CH₂)₂OC₂H₅ |
| Ia41 | CH=CBr—COO(CH₂)₂OCH₃ |
| Ia42 | CH=CBr—COO(CH₂)₂OC₂H₅ |
| Ia43 | CH=CH—COOCH₂CF₃ |
| Ia44 | CH=CCl—COOCH₂CF₃ |
| Ia45 | CH=CBr—COOCH₂CF₃ |
| Ia46 | CH=CI—COOCH₂CF₃ |
| Ia47 | CH=CF—COOCH₂CF₃ |
| Ia48 | CH=CH—COO—N=C(CH₃)₂ |
| Ia49 | CH=CCl—COO—N=C(CH₃)₂ |
| Ia50 | CH=CBr—COO—N=C(CH₃)₂ |

In addition, the following substituted N-phenylglutarimides I are particularly preferred.

the compounds Ib1 to Ib50, which differ from the compounds Ia1 to Ia50 in that $R^2$ is fluorine;

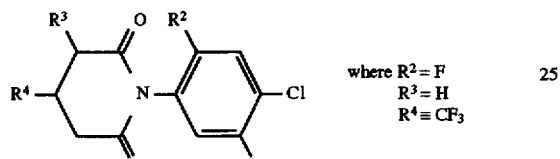

the compounds Ic1 to Ic50, which differ from the compounds Ia1 to Ia50 in that $R^3$ is methyl;

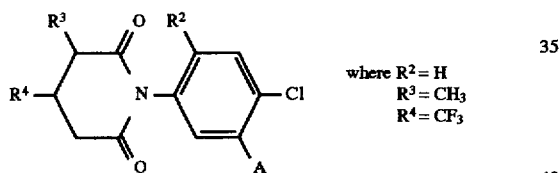

the compounds Id1 to Id50, which differ from the compounds Ia1 to Ia50 in that $R^2$ is fluorine and $R^3$ is methyl;

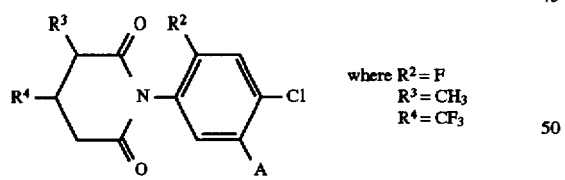

the compounds Ie1 to Ie50, which differ from the compounds Ia1 to Ia50 in that $R^4$ is difluoromethyl;

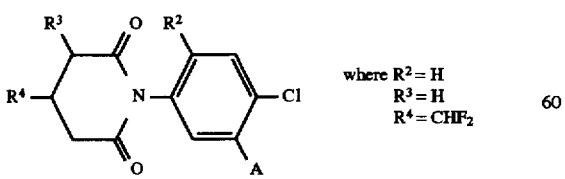

the compounds If1 to If50, which differ from the compounds Ia1 to Ia50 in that $R^2$ is fluorine and $R^4$ is difluoromethyl;

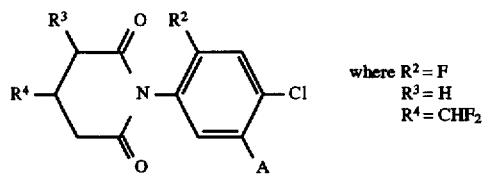

the compounds Ig1 to Ig50, which differ from the compounds Ia1 to Ia50 in that $R^3$ is methyl and $R^4$ is difluoromethyl;

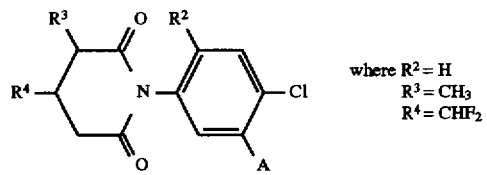

the compounds Ih1 to Ih50, which differ from the compounds Ia1 to Ia50 in that $R^2$ is fluorine, $R^3$ is methyl and $R^4$ is difluoromethyl.

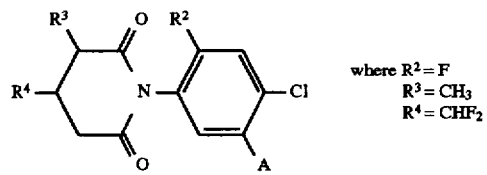

The substituted N-phenylglutarimides I or N-phenylglutaramides II according to the invention and their agriculturally utilizable salts are useful as herbicides, in particular for combating dicotyledon weeds and as defoliants/desiccants, in particular for defoliating cotton, and as defoliants for desiccating the above-ground parts of crop plants, for example potato, sunflower, soybean and rape. Completely mechanized harvesting of these important crop plants is thus made possible.

Of economical interest is also facilitation of harvesting, which is made possible by the falling off or decrease, which is concentrated in terms of time, in the firmness of attachment to the tree in the case of citrus fruits, olives or in other species and types of pomaceous fruit, stone fruit and indehiscent fruit. They additionally lead to a uniform maturation of the harvested fruit.

The same mechanism, i.e. the promotion of the formation of abscission tissue between the fruit or leaf and shoot part of the plant is also essential for a well-controllable defoliation of crop plants such as, in particular, cotton. The shortening of the time interval within which the individual cotton plants become ripe additionally leads to an increased fiber quality after harvesting.

The compounds I and II or the herbicidal agents or desiccants/defoliants containing them can be used, for example, in the form of directly sprayable aqueous solutions, powders, suspensions, also high-percentage aqueous, oily or other suspensions or dispersions, emulsions, oil dispersions, pastes, dusts, broadcasting agents or granules by spraying, nebulizing, atomizing, broadcasting or watering. The application forms depend on the intended applications; they should in each case ensure as fine a dispersion of the active compounds as possible.

The compounds I and II are generally useful for preparing directly sprayable solutions, emulsions, pastes or oil dispersions. Suitable inert additives are mineral oil fractions of average to high boiling point, such as kerosine or diesel oil, and also coal tar oils and oils of vegetable or animal origin, aliphatic, cyclic and aromatic hydrocarbons, eg. toluene, xylene, paraffin, tetrahydronaphthalene, alkylated naphthalenes or their derivatives, methanol, ethanol, propanol, butanol, cyclohexanol, cyclohexanone, chlorobenzene, isophorone or strongly polar solvents, such as N,N-dimethylformamide, dimethyl sulfoxide, N-methylpyrrolidone or water.

Aqueous application forms can be prepared from emulsion concentrates, dispersions, pastes, wettable powders or water-dispersible granules by addition of water. To prepare emulsions, pastes or oil dispersions, the substrates can be homogenized in water, as such or dissolved in an oil or solvent, by means of wetting agents, adherents, dispersants or emulsifiers. However, concentrates consisting of active substance, wetting agent, adherents, dispersant or emulsifier and optionally solvent or oil can also be prepared, which are suitable for dilution with water.

Suitable surface-active substances are the alkali metal, alkaline earth metal and ammonium salts of aromatic sulfonic acids, for example ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, and of fatty alcohol glycol ethers, condensation products of sulfonated naphthalene and its derivatives with formaldehyde, condensation products of naphthalene or of naphthalenesulfonic acids with phenol and formaldehyde, polyoxyethylene octylphenol ethers, ethoxylated isooctyl-, octyl- or nonylphenol, alkylphenol- and tributylphenyl polyglycol ethers, alkylaryl polyether alcohols, isotridecyl alcohol, fatty alcohol ethylene oxide condensates, ethoxylated castor oil, polyoxyethylene alkyl ethers or polyoxypropylene, lauryl alcohol polyglycol ether acetate, sorbitol esters, lignin-sulfite waste liquors or methylcellulose.

Powders, broadcasting agents and dusts can be prepared by mixing or mutual grinding of the active substances with a solid carrier.

Granules, for example coated, impregnated and homogeneous granules can be prepared by binding of the active compounds to solid carriers. Solid carriers are mineral earths such as silica gel, silicic acids, silicates, talc, kaolin, limestone, lime, chalk, bole, loess, clay, dolomite, diatomaceous earth, calcium sulfate and magnesium sulfate, magnesium oxide, ground plastics, fertilizers, such as ammonium sulfate, Ammonium phosphate, ammonium nitrate, ureas and vegetable products, such as cereal meal, tree bark, wood and nut shell meal, cellulose powder or other solid carriers.

The formulations in general contain between 0.01 and 95% by weight, preferably between 0.5 and 90% by weight, of active ingredient. The active ingredients are employed here in a purity of from 90% to 100%, preferably from 95% to 100% (by NMR spectrum).

Examples of such preparations are:

I. a mixture of 20 parts by weight of the compound No. 1.2, 80 parts by weight of xylene, 10 parts by weight of the adduct of 8 to 10 mol of ethylene oxide to 1 mol of oleic acid N-monoethanolamide, 5 parts by weight of calcium salt of dodecylbenzenesulfonic acid, and 5 parts by weight of the adduct of 40 mol of ethylene oxide to i mol of castor oil. By finely dispersing the mixture in 100,000 parts by weight of water, an aqueous dispersion which contains 0.02% by weight of the active ingredient is obtained.

II. a dispersion of 20 parts by weight of the compound No. 1.2 in a mixture of 40 parts by weight of cyclohexanone, 30 parts by weight of isobutanol, 20 parts by weight of the adduct of 7 mol of ethylene oxide to I mol of isooctylphenol and 10 parts by weight of the adduct of 40 mol of ethylene oxide to i mol of castor oil. The mixture of this dispersion with 100,000 parts by weight of water contains 0.02% by weight of the active ingredient.

III. a dispersion of 20 parts by weight of the compound No. 1.5 in a mixture of 25 parts by weight of cyclohexanone, 65 parts by weight of a mineral oil fraction of boiling point 210° to 280° C. and 10 parts by weight of the adduct of 40 mol of ethylene oxide to 1 mol of castor oil. The mixture of this dispersion with 100,000 parts by weight of water contains 0.02% of the active ingredient.

IV. a mixture, ground in a hammer mill, of 20 parts by weight of the compound No. 1.1, 3 parts by weight of the sodium salt of diisobutylnaphthalene-α-sulfonic acid, 17 parts by weight of the sodium salt of a lignosulfonic acid from a sulfite waste liquor and 60 parts by weight of powdered silica gel. By finely dispersing the mixture in 20,000 parts by weight of water, a spray liquor is obtained which contains 0.1% by weight of the active ingredient.

V. a mixture of 3 parts by weight of the compound No. 1.2 and 97 parts by weight of finely divided kaolin. This dust contains 3% by weight of active ingredient.

VI. a stable oily dispersion of 20 parts by weight of the compound No. 1.4, 2 parts by weight of the calcium salt of dodecylbenzenesulfonic acid, 8 parts by weight of fatty alcohol polyglycol ether, 2 parts by weight of the sodium salt of a phenolsulfonic acid urea/formaldehyde condensate and 68 parts by weight of a paraffinic mineral oil.

The application of the herbicidal compositions or of the active ingredients can be carried out pre-emergence or post-emergence. If the active compounds are less tolerable to certain crop plants, application techniques can be used in which the herbicidal compositions are sprayed with the aid of spray equipment such that the leaves of the sensitive crop plants are affected as little as possible, while the active ingredients reach the leaves of undesired plants growing under them or the uncovered soil surface (post-directed, lay-by).

The application amounts of active ingredient are, depending on the combat target, time of year, target plants and growth stage 0.001 to 3.0, preferably 0.01 to 1 kg/ha of active substance (a.s.).

In view of the versatility of the application methods, the compounds I and II or compositions containing them can also be employed in a further number of crop plants for the elimination of undesired plants. Suitable crops are, for example, the following (botanical names):

*Allium cepa, Ananas comosus, Arachis hypogaea, Asparagus officinalis, Beta vulgaris* spp. altissima, *Beta vulgaris* spp. rapa, *Brassica napus* var. napus, *Brassica napus* var. napobrassica, *Brassica rapa* var. silvestris, *Camellia sinensis, Carthamus tinctorius, Carya illinoinensis, Citrus limon, Citrus sinensis, Coffea arabica (Coffea canephora, Coffea liberica), Cucumis sativus, Cymodon dactylon, Daucus carota, Elaeis guineensis, Fragaria vesca, Glycine max, Gossypium hirsutum (Gossypium arboreum, Gossypium herbaceum, Gossypium vitifolium), Helianthus annuus, Hevea brasiliensis, Hordeum vulgare, Humulus lupulus, Ipomoea batatas, Juglans* regia, Lens culinaris, Linum usitatis-simum, Lycopersicon lycopersicum, Malus spp., Manihot esculenta, Medicago sativa, Musa spp., Nicotiana tabacum (N. rustica), Otea europaea Oryza sativa, Phaseolus lunatus, Phaseolus vulgaris, Picea abies, Pinus spp., Pisum sativum, Prunus avium, Prunus persica, Pyrus communis, Ribes sylvestre, Ricinus communis, Saccharum officinarum, Secale cereale, Solanum tuberosum, Sorghum bicolor (S. vulgare), Theobroma cacao, Trifolium pratense, Triticum aestivum, Triticum durum, Vicia faba, Vitis vinifera, Zea mays.

To broaden the spectrum of action and to achieve synergistic effects, the compounds I and II can be applied mixed and together with numerous representatives of other herbicidal or growth-regulating active compound groups. Suitable examples of mixture components are diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives which carry in the 2-position eg. a carboxyl or carboximino group, quinolinecarboxylic acid derivatives, imidazolinones, sulfonamides, sulfonylureas, aryloxy- and heteroaryloxyphenoxypropionic acids and their salts, esters and amides and others.

It may additionally be of use to jointly apply the compounds I and II, oh their own or in combination with other herbicides, also mixed with other plant protection agents, for example with agents for combating pests or phytopathogenic fungi or bacteria. Also of interest is the miscibility with mineral salt solutions, which are employed for eliminating nutritional and trace element deficiencies. However, non-phytotoxic oils and oil concentrates can also be added.

Preparation examples

EXAMPLE 1

N-[4-Chloro-3-(2-chloro-2-ethoxycarbonylethenyl)phenyl]-3-methylglutaric acid monoamide (compound 2.1)

5.2 g of 4-chloro-3-(2-chloro-2-ethoxycarbonyl-ethenyl)aniline in 30 ml of dichloromethane were added dropwise at 25° C. to a solution of 2.56 g of 3-methylglutaric anhydride in 50 ml of dichloromethane. After 3 h, the deposited precipitate was removed and washed with dichloromethane. Yield: 5 g; m.p.: 137°–138° C.

EXAMPLE 2

N-[4-Chloro-3-(2-chloro-2-ethoxycarbonylethenyl)phenyl]-3-methylglutaric acid imide (compound 1.1)

A solution of 2.8 g of N-[4-chloro-3-(2-chloro-2-ethoxycarbonylethenyl)phenyl]-3-methylglutaric acid monoamide and 0.1 g of sodium acetate in 50 ml of acetic anhydride was stirred at 95° C. for 2 h. The solvent was then removed. After dissolving the residue in 150 ml of dichloromethane, it was washed with sodium hydrogencarbonate solution, water and sodium chloride solution, dried and concentrated in vacuo. The residue which remained was crystallized using petroleum ether, and the crystals were removed and dried. Yield: 2.1 g; m.p.: 82°–84° C.

EXAMPLE 3

1-[4-Chloro-3-(2-chloro-2-ethoxycarbonylethenyl)phenyl]-3-trifluoromethyl-6-thiono-(2H)-3,4,5,6-tetrahydropyrid-2-one (Compound 1.7)

1.6 g of Lawesson's reagent*) were added to a solution of 2.1 g of N-[4-chloro-3-(2-chloro-2-ethoxy-carbonylethenyl)phenyl]-3-trifluoromethylglutarimide in 100 ml of toluene. The mixture was heated to reflux temperature for 4 hours and then treated with a further 0.8 g of Lawesson's reagent*). After stirring at reflux temperature for 3 hours the solvent was distilled off. The residue was purified by chromatography on silica gel (eluent: toluene). Yield: 0.6 g of oil.

*) 2,4-bis (4-methoxyphenyl)-1,3,2,4-dithiadiphosphetane-2,4-dione

EXAMPLE 4

Ethyl N-[4-chloro-3-(2-chloro-2-ethoxycarbonylethenyl)phenyl]-3-trifluoromethylglutaramidate 0.13 g (34 mmol) of sodium borohydride was added in portions at room temperature to a solution of 4.2 g (10 mmol) of N-[4-chloro-3-(2-chloro-2-ethoxycarbonylethenyl)phenyl]-3-trifluoromethylglutarimide in 100 ml of ethanol. After stirring for 3 hours the reaction mixture was added to 100 ml of water, after which the aqueous phase was extracted twice with dichloromethane. The combined org. phases were dried over sodium sulfate and concentrated. Finally, the residue was purified by triturating with petroleum ether. Yield: 2 g (42%); m.p.: 115°–117° C.

The active ingredients shown in tables 3 and 4 below were obtained in an analogous manner.

TABLE 3

N-Phenylglutarimides of the formula I ($R^1$ = Cl; $X^2$ = O)

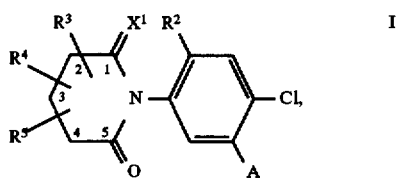

| No. | $X^1$ | $R^2$ | $R^3$ | $R^4$ | $R^5$ | A | M.p. [°C.] |
|---|---|---|---|---|---|---|---|
| 1.01 | O | H | 3-CH$_3$ | H | H | CH=CCl—COOC$_2$H$_5$ | 82–84 |
| 1.02 | O | H | 3-CF$_3$ | H | H | CH=CCl—COOC$_2$H$_5$ | 128–130 |
| 1.03 | O | H | H | H | H | CH=CCl—COOC$_2$H$_5$ | 165–166 |
| 1.04 | O | H | 3-CH$_3$ | 3-CH$_3$ | H | CH=CCl—COOC$_2$H$_5$ | 73–75 |
| 1.05 | O | H | 2-CH$_3$ | 2-CH$_3$ | H | CH=CCl—COOC$_2$H$_5$ | oil |

TABLE 3-continued

N-Phenylglutarimides of the formula I ($R^1$ = Cl; $X^2$ = O)

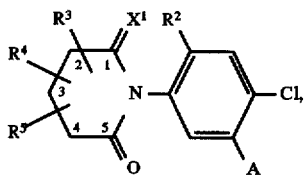

| No. | $X^1$ | $R^2$ | $R^3$ | $R^4$ | $R^5$ | A | M.p. [°C.] |
|---|---|---|---|---|---|---|---|
| 1.06 | O | F | 3-$CF_3$ | H | H | CH=CCl—$COOC_2H_5$ | 101–103 |
| 1.07 | S | H | 3-CF | H | H | CH=CCl—$COOC_2H_5$ | oil |
| 1.08 | O | H | 3-$CF_3$ | 2-$CH_3$ | H | CH=CCl—$COOC_2H_5$ | 123–125 |
| 1.09 | O | H | 3-$OC_2H_5$ | H | H | CH=CCl—$COOC_2H_5$ | oil |
| 1.10 | O | H | —O—$CH_2CH_2$—S— | | H | CH=CCl—$COOC_2H_5$ | 134 |
| 1.11 | O | H | 3-$CF_3$ | H | H | CH=C($CH_3$)—$COOCH_3$ | 130–31 |
| 1.12 | O | H | 3-$CF_3$ | H | H | CH=C(CN)—$COOCH_3$ | |
| 1.13 | O | H | 3-$CF_3$ | H | H | CH=CBr—$COOCH_3$ | |
| 1.14 | O | H | 3-$CF_3$ | H | H | CH=CH—COOCH($CH_3$)$_2$ | |
| 1.15 | O | H | 3-$CF_3$ | H | H | CH=CH—CON($CH_3$)$_2$ | |
| 1.16 | O | H | 3-$CF_3$ | H | H | CH=CCl—$COCH_3$ | |
| 1.17 | O | H | 3-$CF_3$ | H | H | CH=CH—$COCH_2$Cl | |

TABLE 4

N-Phenylgluatric acid monoamides of the formula II (where $X^1$ = O; $R^1$ = Cl; A = —CH=$CR^8$—$COOR^9$)

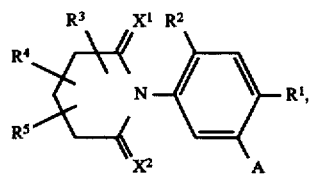

| No. | $R^2$ | $R^3$ | $R^4$ | $R^5$ | $R^8$ | $R^9$ | $R^{12}$ | M.p. [°C.] |
|---|---|---|---|---|---|---|---|---|
| 2.01 | H | 3-$CH_3$ | H | H | Cl | $C_2H_5$ | H | 137–138 |
| 2.02 | H | 3-$CH_3$ | H | H | Cl | $C_2H_5$ | H | 169–170 |
| 2.03 | H | H | H | H | Cl | $C_2H_5$ | H | 116–117 |
| 2.04 | H | 3-$CH_3$ | 3-$CH_3$ | H | Cl | $C_2H_5$ | H | 98–100 |
| 2.05 | H | 2-$CH_3$ | 2-$CH_3$ | H | Cl | $C_2H_5$ | H | 130–131 |
| 2.06 | H | 3-$CF_3$ | H | H | Cl | $C_2H_5$ | i-$C_3H_7$ | 76–78 |
| 2.07 | F | 3-$CF_3$ | H | H | Cl | $C_2H_5$ | H | 143–145 |
| 2.08 | H | 3-$CF_3$ | H | H | Cl | $C_2H_5$ | $C_2H_5$ | 115–117 |
| 2.09 | H | 3-$CF_3$ | 2-$CH_3$ | H | Cl | $C_2H_5$ | H | 168–170 |
| 2.10 | H | 3-$OC_2H_5$ | H | H | Cl | $C_2H_5$ | H | 77 |
| 2.11 | H | 3-$CF_3$ | H | H | $CH_3$ | $CH_3$ | H | 138–140 |

Use examples

The herbicidal action of the substituted N-phenylglutarimides I and N-phenylglutaramides II could be shown by greenhouse experiments:

The crop containers used were plastic flower pots containing loamy sand with about 3.0% by weight of humus as substrate. The seeds of the test plants were sown separately according to species.

In the case of pre-emergence treatment, the active ingredients suspended or eanulsified in water were applied directly after sowing by means of finely distributing nozzles. The containers were lightly watered in order to promote germination and growth and then covered with transparent plastic hoods until the plants had taken root. This covering caused a more uniform germination of the test plants if this was not affected by the active compounds. The application rate for the pre-emergence application was 0.125 or 0.25 kg/ha of a.s. (active substance).

For the purposes of post-emergence treatment, the test plants were each grown, according to growth form, up to a growth height of from 3 to 15 cm and only then treated with the active compounds suspended or emulsified in water. The test plants had either already been sown and raised in the test containers in which they were treated, or they were grown separately as seedlings and transplanted into the test containers some days before treatment with the active ingredient preparations.

The application rate for post-emergence treatment was 0.125 or 0.25 kg/ha of a.s. (active substance).

Depending on species, the plants were kept at temperatures of from 10° to 25° C. or from 20° to 35° C. The test period extended over 2 to 4 weeks. During this time, the plants were tended and their reaction to the individual treatments was assessed.

Assessment was carried out on a scale of from 0 to 100. Here 100 means no emergence of the plants or complete destruction of at least the above-ground parts and 0 no damage or normal course of growth.

The greenhouse tests were carried out on Amaran thusretroflexus, Abutilon theophrasti, Chenopodium album, Matricaria inodora and Veronica subspecies.

The result showed that using compound No. 1.2 undesired weeds can be combated very effectively both post-emergence and pre-emergence.

We claim:

1. Substituted N-phenylglutarimides of the formula I where the variables have the following meanings:
$X^1$, $X^2$
are oxygen or sulfur;
$R^1$
is halogen, nitro, cyano or trifluoromethyl;
$R^2$
is hydrogen or halogen;

$R^3$, $R^4$, $R^5$ independently of one another are hydrogen, halogen, cyano, $C_1$–$C_6$-alkyl, $C_3$–$C_7$-cycloalkyl, $C_2$–$C_6$-alkenyl, $C_2$–$C_6$-alkynyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-cyanoalkyl, $C_1$–$C_6$-alkoxycarbonyl, phenyl or benzyl, where the phenyl group or the phenyl ring of the benzyl group may be substituted by $C_1$–$C_6$-alkyl, $C_1$–$C_6$-alkoxy, halogen, cyano, nitro or trifluoromethyl, or two substituents of a carbon atom of the glutarimide ring are bonded to one another via a 2- to 5-membered chain and thus form a spiro ring, which, if desired, can carry one or two halogen atoms, the spiro ring in addition to the C atoms also being able to contain one or two non-adjacent ring members selected from the group consisting of —O—, —S—, —NH— and —N($C_1$–$C_4$-alkyl)—, or two substituents of two adjacent carbon atoms of the glutarimide ring are bonded to one another via a 1- to 5-membered chain and thus form a fused ring, which, if desired, can carry one or two halogen atoms, the fused ring in addition to the C atoms also being able to contain one or two non-adjacent ring members selected from the group consisting of —O—, —S—, —NH— and —N($C_1$–$C_4$-alkyl)—;

A is $CHR^6$—$CHR^7$—CO—B or $CR^6$=$CR^8$—CO—B, where $R^6$ is hydrogen, $C_1$–$C_6$-alkyl or $C_1$–$C_6$-haloalkyl;

$R^7$ is halogen, $C_1$–$C_6$-haloalkyl, hydroxyl, $C_1$–$C_6$-alkoxy or $C_1$–$C_6$-alkylcarbonyloxy, and $R^8$ is hydrogen, halogen, cyano, $C_1$–$C_6$-alkyl, $C_1$–$C_6$-haloalkyl, hydroxyl, $C_1$–$C_6$-alkoxy, $C_1$–$C_6$-alkylcarbonyl, $C_1$–$C_6$-alkoxycarbonyl or $C_1$–$C_6$-alkylcarbonyloxy and where B has one of the following meanings:

(a) is hydrogen, (b) is $C_1$–$C_6$-alkyl, $C_3$–$C_6$-alkenyl, $C_3$–$C_6$-alkynyl, $C_1$–$C_6$-haloalkyl, $C_3$–$C_7$-cycloalkyl, $C_1$–$C_6$-alkoxy-$C_1$–$C_6$-alkyl, $C_1$–$C_6$-dialkoxy-$C_1$–$C_6$-alkyl or $C_1$–$C_6$-alkylthio-$C_1$–$C_6$-alkyl;

(c) is $OR^9$, $SR^9$, where $R^9$ is:

hydrogen, $C_1$–$C_6$-alkyl, $C_3$–$C_6$-alkenyl, $C_3$–$C_6$-alkynyl, $C_3$–$C_7$-cycloalkyl, halo-$C_1$–$C_6$-alkyl, $C_1$–$C_6$-cyanoalkyl, $C_3$–$C_6$-haloalkenyl, $C_1$–$C_6$-alkoxycarbonyl-$C_1$–$C_6$-alkyl, $C_1$–$C_6$-alkoxy-$C_1$–$C_6$-alkyl, $C_1$–$C_6$-alkylthio-$C_1$–$C_6$-alkyl, $C_1$–$C_6$-alkylimino or $C_1$–$C_6$-alkyloximino-$C_1$–$C_6$-alkyl, phenyl, phenyl substituted by one or more $C_1$–$C_6$-alkyl, $C_3$–$C_6$-alkenyl, halogen, cyano, nitro, $C_1$–$C_6$-alkoxy or $C_1$–$C_6$-alkoxycarbonyl radicals, benzyl or benzyl substituted by one or more $C_1$–$C_6$-alkyl, $C_3$–$C_6$-alkenyl, halogen, cyano, nitro, $C_1$–$C_6$-alkoxy or $C_1$–$C_6$-alkoxycarbonyl radicals;

(d) is $NR^{10}R^{11}$, where $R^{10}$ and $R^{11}$ independently of one another have the following meanings:

hydrogen, $C_1$–$C_6$-alkyl, $C_3$–$C_6$-alkenyl, $C_3$–$C_6$-alkynyl, $C_3$–$C_7$-cycloalkyl, $C_1$–$C_6$-haloalkyl, $C_1$–$C_6$-alkylcarbonyl, $C_1$–$C_6$-alkoxycarbonyl, $C_1$–$C_6$-alkoxy-$C_1$–$C_6$-alkyl, phenyl, phenyl substituted by one to three $C_1$–$C_6$-alkyl, $C_3$–$C_6$-alkenyl, halogen, cyano, nitro, $C_1$–$C_6$-alkoxy or $C_1$–$C_6$-alkoxycarbonyl radicals, or $R^{10}$ and $R^{11}$, together with the nitrogen atom to which they are bonded, are a saturated or unsaturated 4- to 7-membered heterocycle having one or two further identical or different heteroatoms selected from the group consisting of nitrogen, oxygen and sulfur;

and the agriculturally utilizable salts of the substituted N-phenylglutarimides I.

2. Substituted N-phenylglutarimides of the formula I as defined in claim 1, in which $R^4$ is $C_1$–$C_6$-alkyl or $C_1$–$C_6$-haloalkyl and $R^3$ and $R^5$ are hydrogen or $C_1$–$C_4$-alkyl.

3. Substituted N-phenylglutarimides of the formula I'

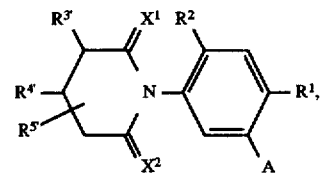

where $R^{4'}$ is $C_1$–$C_6$-haloalkyl, $R^{3'}$ and $R^{5'}$ independently of one another are hydrogen, $C_1$–$C_6$-alkyl or $C_1$–$C_6$-haloalkyl and A, $X^1$ and $X^2$ are as defined in claim 1.

4. Substituted N-phenylglutarimides of the formula I' as defined in claim 3, where $R^4$ is trichloromethyl, difluoromethyl, trifluoromethyl, pentafluoroethyl or difluorochloromethyl.

5. Substituted N-phenylglutarimides of the formula I as defined in claim 1, where $R^1$ is halogen.

6. Substituted N-phenylglutarimides of the formula I as defined in claim 1, where $R^2$ is hydrogen, fluorine or chlorine.

7. Substituted N-phenylglutarimides of the formula I as defined in claim 1, where A is $CHR^6$—$CHR^7$—CO—B.

8. Substituted N-phenylglutarimides of the formula I as defined in claim 1, where A is $CR^6$=$CR^8$—CO—B.

9. N-Phenylglutaramides of the formula II

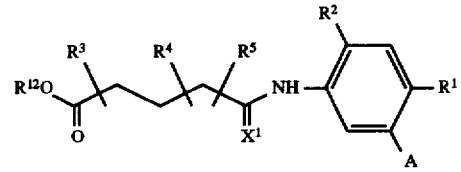

where $X^1$, $R^1$, $R^2$, $R^3$, $R^4$, $R^5$ and A have the meanings mentioned in claim 1 and $R^{12}$ is hydrogen, $C_1$–$C_6$-alkyl or benzyl, and the agriculturally utilizable salts of the N-phenylglutaramides II.

10. A herbicidal composition or composition for the desiccation and/or defoliation of plants, containing an inert liquid or solid carrier and an amount of at least one substituted N-phenylglutarimide of the formula I or an agriculturally utilizable salt of I as defined in claim 1, which is herbicidally active or has desiccant and/or defoliant activity.

11. A method for combating undesired plant growth, which comprises allowing an amount of at least one substituted N-phenylglutarimide of the formula I or an agriculturally utilizable salt of I as defined in claim 1 which is herbicidally active to act on plants, their environment or on seeds.

12. A method for desiccation and/or defoliation of plants, which comprises allowing an amount of at least one substituted N-phenylglutarimide of the formula I or an agriculturally utilizable salt of I as defined in claim 1 which has desiccant and/or defoliant activity to act on plants.

13. A process for preparing substituted N-phenylglutarimides of the formula I as defined in claim 1

(a) in formula I where $X^1$=oxygen or sulfur and $X^2$=oxygen, which comprises cyclizing an N-phenylglutaramide of the formula II

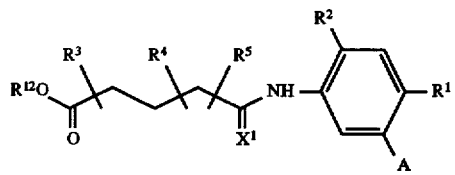

where $X^1$, $R^1$, $R^2$, $R^3$, $R^4$, $R^5$ and A have the meanings mentioned in claim 1, and where $R^{12}$ is hydrogen, in the presence of a dehydrating agent;

b) in formula I where $X^1$=oxygen or sulfur and $X^2$=oxygen, which comprises cyclizing an N-phenylglutaric amide of the formula II

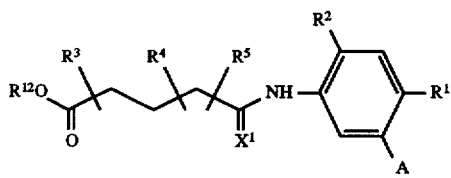

where $X^1$, $R^1$, $R^2$, $R^3$, $R^4$, $R^5$ and A have the meanings mentioned in claim 1, and where $R^{12}$ is not hydrogen;

c) in formula I where $X^1$=sulfur and $X^2$=oxygen or sulfur, which comprises reacting an N-phenylglutarimide of the formula I, where $X^1$ is oxygen,

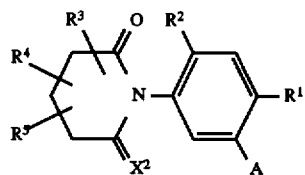

with a suitable sulfurizing reagent.

* * * * *

UNITED STATES PATENT AND TRADEMARK OFFICE
CERTIFICATE OF CORRECTION

PATENT NO. : 5,698,494
DATED : December 16, 1997
INVENTOR(S) : KLINTZ et al.

It is certified that error appears in the above-identified patent and that said Letters Patent is hereby corrected as shown below:

On the cover page, in the abstract, item [57], "cytoalkyl" should be --cycloalkyl--.

On the cover page, in the abstract, item [57], after "alkoxycarbonyl or" insert --$R^7$--.

Signed and Sealed this

Seventeenth Day of March, 1998

BRUCE LEHMAN

*Attest:*

*Attesting Officer*  *Commissioner of Patents and Trademarks*